US010342675B2

(12) United States Patent
Alheidt

(10) Patent No.: US 10,342,675 B2
(45) Date of Patent: Jul. 9, 2019

(54) EXPANDABLE IMPLANT

(71) Applicant: Stryker European Holdings I, LLC, Kalamazoo, MI (US)

(72) Inventor: Thomas A. Alheidt, Sussex, NJ (US)

(73) Assignee: Stryker European Holdings I, LLC, Kalamazoo, MI (US)

(*) Notice: Subject to any disclaimer, the term of this patent is extended or adjusted under 35 U.S.C. 154(b) by 2 days.

(21) Appl. No.: 14/196,548

(22) Filed: Mar. 4, 2014

(65) Prior Publication Data

US 2014/0257486 A1 Sep. 11, 2014

Related U.S. Application Data

(60) Provisional application No. 61/775,909, filed on Mar. 11, 2013.

(51) Int. Cl.
*A61F 2/44* (2006.01)
*A61F 2/46* (2006.01)
(Continued)

(52) U.S. Cl.
CPC ............ *A61F 2/447* (2013.01); *A61F 2/4455* (2013.01); *A61F 2/4611* (2013.01);
(Continued)

(58) Field of Classification Search
CPC ........ A61F 2/44; A61F 2/4455; A61F 2/4465; A61F 2/4611; A61F 2/447;
(Continued)

(56) References Cited

U.S. PATENT DOCUMENTS 2,799,196 A 7/1957 Alvarez
3,426,364 A 2/1969 Lumb
(Continued)

FOREIGN PATENT DOCUMENTS

CA 1333209 C 11/1994
DE 3729600 A1 3/1989
(Continued)

OTHER PUBLICATIONS

Wave Plif Cage, "Product Information: The Expandable Lumbar Cage", Advanced Medical Technologies AG (date unkown.).
(Continued)

*Primary Examiner* — Eric S Gibson
*Assistant Examiner* — Marcela I Shirsat
(74) *Attorney, Agent, or Firm* — Lerner, David, Littenberg, Krumholz & Mentlik, LLP

(57) ABSTRACT

An expandable implant system is disclosed in which the system comprises an implant with: (1) top and bottom plates, (2) ramp surfaces formed on inner surfaces of the plates, and (3) an expansion member situated between the plates. An actuator also forms part of the system, the actuator being removable from between the top and bottom plates after implantation of the implant. The expansion member has a set of angled surfaces for mating with the ramp surfaces of the plates and, upon movement of the expansion member along a longitudinal axis of the implant, the top and bottom plates expand from a first dimension to a second greater dimension. The top and bottom plates are also securable at varying angles to one another depending on the amount of movement of the expansion member along the ramp surfaces.

25 Claims, 5 Drawing Sheets

(51) Int. Cl.
*A61F 2/28* (2006.01)
*A61F 2/30* (2006.01)

(52) U.S. Cl.
CPC ............... *A61F 2002/2835* (2013.01); *A61F 2002/30136* (2013.01); *A61F 2002/30281* (2013.01); *A61F 2002/30466* (2013.01); *A61F 2002/30494* (2013.01); *A61F 2002/30556* (2013.01); *A61F 2002/30578* (2013.01); *A61F 2002/30579* (2013.01); *A61F 2002/30772* (2013.01); *A61F 2002/30774* (2013.01); *A61F 2002/30904* (2013.01); *A61F 2002/4475* (2013.01)

(58) Field of Classification Search
CPC .. A61F 2002/30579; A61F 2002/30466; A61F 2002/4475; A61F 2002/30556; A61F 2002/30281; A61F 2002/30578
USPC ............................................. 623/17.11–17.16
See application file for complete search history.

(56) References Cited

U.S. PATENT DOCUMENTS

| | | | |
|---|---|---|---|
| 3,486,505 A | 12/1969 | Morrison | |
| 4,309,777 A | 1/1982 | Patil | |
| 4,401,112 A | 8/1983 | Rezaian | |
| 4,522,200 A | 6/1985 | Stednitz | |
| 4,545,374 A | 10/1985 | Jacobson | |
| 4,553,273 A | 11/1985 | Wu | |
| 4,599,086 A | 7/1986 | Doty | |
| 4,636,217 A | 1/1987 | Ogilvie et al. | |
| 4,657,550 A | 4/1987 | Daher | |
| 4,733,665 A | 3/1988 | Palmaz | |
| 4,863,476 A | 9/1989 | Shepperd | |
| 4,878,915 A | 11/1989 | Brantigan | |
| 4,932,375 A | 6/1990 | Burney | |
| 4,932,969 A | 6/1990 | Frey et al. | |
| 4,936,851 A | 6/1990 | Fox et al. | |
| 4,946,378 A | 8/1990 | Hirayama et al. | |
| 5,059,193 A | 10/1991 | Kuslich | |
| 5,171,278 A | 12/1992 | Pisharodi | |
| 5,192,327 A | 3/1993 | Brantigan | |
| 5,236,460 A | 8/1993 | Barber | |
| 5,344,252 A | 9/1994 | Kakimoto | |
| 5,390,683 A | 2/1995 | Pisharodi | |
| 5,425,772 A | 6/1995 | Brantigan | |
| 5,484,437 A | 1/1996 | Michelson | |
| 5,522,899 A | 6/1996 | Michelson | |
| 5,554,191 A * | 9/1996 | Lahille ............... A61B 17/1757 411/55 |
| 5,562,736 A | 10/1996 | Ray et al. | |
| 5,571,190 A | 11/1996 | Ulrich et al. | |
| 5,571,192 A | 11/1996 | Schonhoffer | |
| 5,593,409 A | 1/1997 | Michelson | |
| 5,609,635 A | 3/1997 | Michelson | |
| 5,653,762 A | 8/1997 | Pisharodi | |
| 5,653,763 A | 8/1997 | Errico et al. | |
| 5,658,335 A | 8/1997 | Allen | |
| 5,665,122 A | 9/1997 | Kambin | |
| 5,693,100 A | 12/1997 | Pisharodi | |
| 5,702,453 A | 12/1997 | Rabbe et al. | |
| 5,772,661 A | 6/1998 | Michelson | |
| 5,776,197 A | 7/1998 | Rabbe et al. | |
| 5,776,199 A | 7/1998 | Michelson | |
| 5,782,832 A | 7/1998 | Larsen et al. | |
| 5,865,848 A | 2/1999 | Baker | |
| 5,888,228 A | 3/1999 | Knothe et al. | |
| 5,893,889 A | 4/1999 | Harrington | |
| 5,893,890 A | 4/1999 | Pisharodi | |
| 5,972,015 A | 10/1999 | Scribner et al. | |
| 5,980,522 A | 11/1999 | Koros et al. | |
| 6,015,436 A | 1/2000 | Schonhoffer | |
| 6,039,761 A | 3/2000 | Li et al. | |
| 6,045,579 A | 4/2000 | Hochshuler et al. | |
| 6,080,155 A | 6/2000 | Michelson | |
| 6,080,193 A | 6/2000 | Hochshuler et al. | |
| 6,083,225 A | 7/2000 | Winslow et al. | |
| 6,083,228 A | 7/2000 | Michelson | |
| 6,090,143 A | 7/2000 | Meriwether et al. | |
| 6,093,207 A | 7/2000 | Pisharodi | |
| 6,102,949 A | 8/2000 | Biedermann et al. | |
| 6,102,950 A * | 8/2000 | Vaccaro ............... A61F 2/4611 606/247 |
| 6,113,638 A | 9/2000 | Williams et al. | |
| 6,117,174 A * | 9/2000 | Nolan ............... A61F 2/4455 606/247 |
| 6,127,597 A | 10/2000 | Beyar et al. | |
| 6,156,037 A | 12/2000 | LeHuec et al. | |
| 6,159,244 A | 12/2000 | Suddaby | |
| 6,159,245 A | 12/2000 | Meriwether et al. | |
| 6,174,334 B1 | 1/2001 | Suddaby | |
| 6,176,882 B1 | 1/2001 | Biedermann et al. | |
| 6,183,517 B1 | 2/2001 | Suddaby | |
| 6,190,414 B1 | 2/2001 | Young et al. | |
| 6,193,756 B1 | 2/2001 | Studer et al. | |
| 6,193,757 B1 | 2/2001 | Foley et al. | |
| 6,206,923 B1 | 3/2001 | Boyd et al. | |
| 6,210,412 B1 | 4/2001 | Michelson | |
| 6,217,579 B1 | 4/2001 | Koros | |
| 6,224,604 B1 | 5/2001 | Suddaby | |
| 6,245,107 B1 | 6/2001 | Ferree | |
| 6,280,456 B1 | 8/2001 | Scribner et al. | |
| 6,287,308 B1 | 9/2001 | Betz et al. | |
| 6,302,914 B1 | 10/2001 | Michelson | |
| 6,328,738 B1 | 12/2001 | Suddaby | |
| 6,332,895 B1 | 12/2001 | Suddaby | |
| 6,344,057 B1 | 2/2002 | Rabbe et al. | |
| 6,368,351 B1 | 4/2002 | Glenn et al. | |
| 6,395,031 B1 | 5/2002 | Foley et al. | |
| 6,395,032 B1 | 5/2002 | Gauchet | |
| 6,395,034 B1 | 5/2002 | Suddaby | |
| 6,402,750 B1 | 6/2002 | Atkinson et al. | |
| 6,409,766 B1 | 6/2002 | Brett | |
| 6,432,140 B1 | 8/2002 | Lin | |
| 6,436,103 B1 | 8/2002 | Suddaby | |
| 6,436,140 B1 * | 8/2002 | Liu ............... A61F 2/446 623/17.11 |
| 6,443,989 B1 | 9/2002 | Jackson | |
| 6,443,990 B1 | 9/2002 | Aebi et al. | |
| 6,447,544 B1 | 9/2002 | Michelson | |
| 6,447,547 B1 | 9/2002 | Michelson | |
| 6,451,052 B1 | 9/2002 | Burmeister et al. | |
| 6,454,806 B1 | 9/2002 | Cohen et al. | |
| 6,454,807 B1 * | 9/2002 | Jackson ............... A61F 2/447 623/17.15 |
| 6,478,823 B1 | 11/2002 | Michelson | |
| 6,491,724 B1 | 12/2002 | Ferree | |
| 6,527,803 B1 | 3/2003 | Crozet et al. | |
| D472,632 S | 4/2003 | Anderson | |
| D472,633 S | 4/2003 | Anderson | |
| 6,562,074 B2 | 5/2003 | Gerbec et al. | |
| 6,576,016 B1 | 6/2003 | Hochshuler et al. | |
| 6,582,431 B1 | 6/2003 | Ray | |
| 6,582,451 B1 | 6/2003 | Marucci et al. | |
| 6,582,461 B1 | 6/2003 | Burmeister et al. | |
| 6,582,467 B1 | 6/2003 | Teitelbaum et al. | |
| 6,592,625 B2 | 7/2003 | Cauthen | |
| 6,595,998 B2 | 7/2003 | Johnson et al. | |
| 6,610,089 B1 | 8/2003 | Liu et al. | |
| 6,626,905 B1 | 9/2003 | Schmiel et al. | |
| 6,641,614 B1 | 11/2003 | Wagner et al. | |
| 6,648,917 B2 | 11/2003 | Gerbec et al. | |
| 6,666,891 B2 | 12/2003 | Boehm, Jr. et al. | |
| 6,679,915 B1 | 1/2004 | Cauthen | |
| 6,685,742 B1 | 2/2004 | Jackson | |
| 6,706,070 B1 | 3/2004 | Wagner et al. | |
| 6,719,796 B2 | 4/2004 | Cohen et al. | |
| 6,723,126 B1 | 4/2004 | Berry | |
| 6,733,535 B2 | 5/2004 | Michelson | |
| 6,743,255 B2 | 6/2004 | Ferree | |
| 6,758,849 B1 | 7/2004 | Michelson | |
| 6,773,460 B2 | 8/2004 | Jackson | |

(56) References Cited

U.S. PATENT DOCUMENTS

| | | |
|---|---|---|
| 6,814,754 B2 | 11/2004 | Greenhalgh |
| 6,814,756 B1 | 11/2004 | Michelson |
| 6,821,298 B1 | 11/2004 | Jackson |
| 6,833,006 B2 | 12/2004 | Foley et al. |
| 6,835,206 B2 | 12/2004 | Jackson |
| 6,837,850 B2 | 1/2005 | Suddaby |
| 6,840,944 B2 | 1/2005 | Suddaby |
| 6,843,804 B2 | 1/2005 | Bryan |
| 6,852,129 B2 | 2/2005 | Gerbec et al. |
| 6,863,673 B2 | 3/2005 | Gerbec et al. |
| 6,875,173 B2 | 4/2005 | Suddaby |
| 6,893,464 B2 | 5/2005 | Kiester |
| 6,902,568 B2 | 6/2005 | Serhan |
| 6,923,810 B1 | 8/2005 | Michelson |
| 6,953,477 B2 | 10/2005 | Berry |
| 6,955,691 B2 | 10/2005 | Chae et al. |
| 6,962,606 B2 | 11/2005 | Michelson |
| 7,018,415 B1 | 3/2006 | McKay |
| 7,066,961 B2 | 6/2006 | Michelson |
| 7,070,598 B2 | 7/2006 | Lim et al. |
| 7,083,650 B2 | 8/2006 | Moskowitz et al. |
| 7,087,055 B2 | 8/2006 | Lim et al. |
| 7,094,257 B2 | 8/2006 | Mujwid et al. |
| 7,097,648 B1 | 8/2006 | Globerman et al. |
| 7,128,760 B2 | 10/2006 | Michelson |
| 7,204,853 B2 | 4/2007 | Gordon et al. |
| 7,214,243 B2 | 5/2007 | Taylor |
| 7,217,291 B2 | 5/2007 | Zucherman et al. |
| 7,220,280 B2 | 5/2007 | Kast et al. |
| D553,742 S | 10/2007 | Park |
| 7,282,063 B2 | 10/2007 | Cohen et al. |
| 7,306,626 B2 | 12/2007 | Whelan |
| 7,311,733 B2 | 12/2007 | Metz-Stavenhagen |
| 7,316,714 B2 | 1/2008 | Gordon et al. |
| 7,326,250 B2 | 2/2008 | Beaurain et al. |
| 7,326,251 B2 | 2/2008 | McCombe et al. |
| 7,331,996 B2 | 2/2008 | Sato et al. |
| 7,503,933 B2 | 3/2009 | Michelson |
| 7,569,074 B2 | 8/2009 | Eisermann et al. |
| 7,618,456 B2 | 11/2009 | Mathieu et al. |
| 7,618,458 B2 | 11/2009 | Biedermann et al. |
| 7,621,951 B2 | 11/2009 | Glenn et al. |
| 7,655,042 B2 | 2/2010 | Foley et al. |
| 7,674,297 B2 | 3/2010 | Falahee |
| 7,678,148 B2 | 3/2010 | Peterman |
| 7,708,778 B2 | 5/2010 | Gordon et al. |
| 7,708,779 B2 | 5/2010 | Edie et al. |
| 7,727,280 B2 * | 6/2010 | McLuen ............ A61F 2/4455 623/17.16 |
| 7,731,751 B2 | 6/2010 | Butler et al. |
| 7,731,752 B2 | 6/2010 | Edie et al. |
| 7,753,958 B2 | 7/2010 | Gordon et al. |
| 7,789,914 B2 | 9/2010 | Michelson |
| 7,794,501 B2 | 9/2010 | Edie et al. |
| 7,824,445 B2 | 11/2010 | Biro et al. |
| 7,837,734 B2 | 11/2010 | Zucherman et al. |
| 7,850,733 B2 * | 12/2010 | Baynham ............ A61F 2/447 623/17.11 |
| 7,879,098 B1 * | 2/2011 | Simmons, Jr. ........ A61F 2/4465 623/17.11 |
| 7,909,830 B2 | 3/2011 | Frigg et al. |
| 7,909,869 B2 | 3/2011 | Gordon et al. |
| 7,985,256 B2 | 7/2011 | Grotz et al. |
| 8,021,430 B2 | 9/2011 | Michelson |
| 8,062,375 B2 | 11/2011 | Glerum et al. |
| 8,070,813 B2 | 12/2011 | Grotz et al. |
| 8,096,994 B2 | 1/2012 | Phan et al. |
| 8,105,358 B2 | 1/2012 | Phan |
| 8,105,382 B2 | 1/2012 | Olmos et al. |
| 8,118,870 B2 | 2/2012 | Gordon et al. |
| 8,118,871 B2 | 2/2012 | Gordon et al. |
| 8,123,810 B2 | 2/2012 | Gordon et al. |
| 8,147,550 B2 | 4/2012 | Gordon et al. |
| 8,172,903 B2 | 5/2012 | Gordon et al. |
| 8,187,331 B2 | 5/2012 | Strohkirch, Jr. et al. |
| D664,252 S | 7/2012 | Weiland et al. |
| 8,257,440 B2 | 9/2012 | Gordon et al. |
| 8,267,939 B2 | 9/2012 | Cipoletti et al. |
| 8,273,124 B2 | 9/2012 | Renganath et al. |
| 8,273,126 B2 | 9/2012 | Lindner |
| 8,303,662 B2 | 11/2012 | Landry et al. |
| 8,303,663 B2 | 11/2012 | Jimenez et al. |
| 8,328,818 B1 | 12/2012 | Seifert et al. |
| 8,337,558 B2 | 12/2012 | Lindner |
| 8,366,777 B2 | 2/2013 | Matthis et al. |
| 8,394,143 B2 | 3/2013 | Grotz et al. |
| 8,435,296 B2 | 5/2013 | Kadaba et al. |
| 8,454,695 B2 | 6/2013 | Grotz et al. |
| 8,480,741 B2 | 7/2013 | Grotz et al. |
| 8,568,481 B2 | 10/2013 | Olmos et al. |
| 2001/0032020 A1 | 10/2001 | Besselink |
| 2002/0045945 A1 * | 4/2002 | Liu ............ A61F 2/446 623/17.16 |
| 2002/0052656 A1 | 5/2002 | Michelson |
| 2002/0068974 A1 | 6/2002 | Kuslich et al. |
| 2002/0068977 A1 * | 6/2002 | Jackson ............ A61F 2/4455 623/17.15 |
| 2002/0082696 A1 | 6/2002 | Harms et al. |
| 2002/0128716 A1 | 9/2002 | Cohen et al. |
| 2002/0138146 A1 | 9/2002 | Jackson |
| 2003/0004575 A1 | 1/2003 | Erickson |
| 2003/0040798 A1 | 2/2003 | Michelson |
| 2003/0065396 A1 | 4/2003 | Michelson |
| 2003/0135279 A1 | 7/2003 | Michelson |
| 2003/0149482 A1 | 8/2003 | Michelson |
| 2003/0171813 A1 | 9/2003 | Kiester |
| 2003/0195630 A1 | 10/2003 | Ferree |
| 2003/0208263 A1 | 11/2003 | Burmeister et al. |
| 2003/0208270 A9 | 11/2003 | Michelson |
| 2003/0208272 A1 | 11/2003 | Crozet et al. |
| 2003/0208275 A1 | 11/2003 | Michelson |
| 2003/0220650 A1 | 11/2003 | Major et al. |
| 2003/0236520 A1 | 12/2003 | Lim et al. |
| 2004/0010312 A1 | 1/2004 | Enayati |
| 2004/0010315 A1 | 1/2004 | Song |
| 2004/0024460 A1 | 2/2004 | Ferree |
| 2004/0024463 A1 | 2/2004 | Thomas et al. |
| 2004/0030387 A1 | 2/2004 | Landry et al. |
| 2004/0044411 A1 | 3/2004 | Suddaby |
| 2004/0078080 A1 | 4/2004 | Thramann et al. |
| 2004/0087947 A1 | 5/2004 | Lim et al. |
| 2004/0087948 A1 | 5/2004 | Suddaby |
| 2004/0102774 A1 | 5/2004 | Trieu |
| 2004/0153156 A1 | 8/2004 | Cohen et al. |
| 2004/0199252 A1 | 10/2004 | Sears et al. |
| 2004/0215342 A1 | 10/2004 | Suddaby |
| 2004/0225360 A1 | 11/2004 | Malone |
| 2004/0243240 A1 | 12/2004 | Beaurain et al. |
| 2004/0254643 A1 | 12/2004 | Jackson |
| 2004/0254644 A1 | 12/2004 | Taylor |
| 2005/0004673 A1 | 1/2005 | Kluger |
| 2005/0015149 A1 | 1/2005 | Michelson |
| 2005/0015150 A1 | 1/2005 | Lee |
| 2005/0027358 A1 | 2/2005 | Suddaby |
| 2005/0038512 A1 | 2/2005 | Michelson |
| 2005/0049590 A1 | 3/2005 | Alleyne et al. |
| 2005/0060036 A1 | 3/2005 | Schultz et al. |
| 2005/0070911 A1 | 3/2005 | Carrison et al. |
| 2005/0071007 A1 | 3/2005 | Malek |
| 2005/0113842 A1 | 5/2005 | Bertagnoli et al. |
| 2005/0113920 A1 | 5/2005 | Foley et al. |
| 2005/0273171 A1 | 12/2005 | Gordon et al. |
| 2005/0278026 A1 | 12/2005 | Gordon et al. |
| 2006/0022180 A1 | 2/2006 | Selness |
| 2006/0064169 A1 | 3/2006 | Ferree |
| 2006/0116767 A1 | 6/2006 | Magerl et al. |
| 2006/0122701 A1 | 6/2006 | Kiester |
| 2006/0129244 A1 | 6/2006 | Ensign |
| 2006/0149385 A1 | 7/2006 | McKay |
| 2006/0206207 A1 * | 9/2006 | Dryer ............ A61F 2/446 623/17.11 |
| 2006/0224241 A1 | 10/2006 | Butler et al. |
| 2006/0241643 A1 | 10/2006 | Lim et al. |
| 2006/0241764 A1 | 10/2006 | Michelson |

(56) References Cited

U.S. PATENT DOCUMENTS

| | | |
|---|---|---|
| 2006/0247770 A1 | 11/2006 | Peterman |
| 2006/0253201 A1 | 11/2006 | McLuen |
| 2008/0058931 A1 | 3/2008 | White et al. |
| 2008/0071279 A1 | 3/2008 | Bandeira et al. |
| 2008/0082173 A1 | 4/2008 | Delurio et al. |
| 2008/0140207 A1 | 6/2008 | Olmos et al. |
| 2008/0183204 A1 | 7/2008 | Greenhalgh et al. |
| 2009/0222100 A1* | 9/2009 | Cipoletti ............... A61F 2/447 623/17.16 |
| 2010/0017965 A1 | 1/2010 | Barthelt |
| 2010/0049325 A1 | 2/2010 | Biedermann et al. |
| 2010/0145455 A1 | 6/2010 | Simpson et al. |
| 2010/0211176 A1 | 8/2010 | Greenhalgh |
| 2010/0280616 A1 | 11/2010 | Frasier |
| 2010/0286779 A1 | 11/2010 | Thibodeau |
| 2010/0286780 A1 | 11/2010 | Dryer et al. |
| 2010/0292796 A1 | 11/2010 | Greenhalgh et al. |
| 2010/0331985 A1 | 12/2010 | Gordon et al. |
| 2011/0130838 A1 | 6/2011 | Morgenstern Lopez |
| 2011/0172774 A1* | 7/2011 | Varela ................. A61F 2/447 623/17.16 |
| 2012/0035729 A1 | 2/2012 | Glerum et al. |
| 2012/0071982 A1 | 3/2012 | Michelson |
| 2012/0191194 A1 | 7/2012 | Olmos et al. |
| 2012/0290094 A1 | 11/2012 | Lim et al. |
| 2012/0310349 A1 | 12/2012 | Gordon et al. |
| 2012/0316652 A1 | 12/2012 | Renganath et al. |

FOREIGN PATENT DOCUMENTS

| | | |
|---|---|---|
| DE | 102005022920 A1 | 11/2006 |
| EP | 0260044 A1 | 3/1988 |
| EP | 0269175 A2 | 6/1988 |
| EP | 0566807 A1 | 10/1993 |
| EP | 0637439 A1 | 2/1995 |
| EP | 0664994 A1 | 8/1995 |
| EP | 0669114 A1 | 8/1995 |
| EP | 0734702 A1 | 10/1996 |
| EP | 1293180 A1 | 3/2003 |
| GB | 2083754 A | 3/1982 |
| GB | 2219060 A | 11/1989 |
| JP | 62164458 A | 7/1987 |
| JP | 63158045 A | 7/1988 |
| JP | 5208029 A | 8/1993 |
| SU | 01124955 A1 | 11/1984 |
| SU | 01560184 A1 | 4/1990 |
| WO | 9000037 A1 | 1/1990 |
| WO | 9428824 A2 | 12/1994 |
| WO | 9525485 A1 | 9/1995 |
| WO | 9532673 A1 | 12/1995 |
| WO | 9614809 A1 | 5/1996 |
| WO | 9627321 A2 | 9/1996 |
| WO | 9627345 A2 | 9/1996 |
| WO | 9639988 A2 | 12/1996 |
| WO | 9640015 A1 | 12/1996 |
| WO | 9640016 A2 | 12/1996 |
| WO | 9640019 A1 | 12/1996 |
| WO | 9640020 A1 | 12/1996 |
| WO | 9913806 A1 | 3/1999 |
| WO | 2002009626 A1 | 2/2002 |
| WO | 03003951 A1 | 1/2003 |
| WO | 03092507 A2 | 11/2003 |
| WO | 2004047691 A1 | 6/2004 |
| WO | 2004080356 A2 | 9/2004 |
| WO | 2006034436 A2 | 3/2006 |
| WO | 2006037013 A1 | 4/2006 |
| WO | 2006042334 A2 | 4/2006 |
| WO | 2006068682 A1 | 6/2006 |
| WO | 2006116760 A2 | 11/2006 |
| WO | 2006116761 A2 | 11/2006 |
| WO | 2007009107 A2 | 1/2007 |
| WO | 2007041665 A2 | 4/2007 |
| WO | 2010148112 A1 | 12/2010 |

OTHER PUBLICATIONS

Milton, AIPLA quarterly Journal, vol. 34, No. 3, p. 333-358, Summer 2006.

International Search Report and Written Opinion for Application No. PCT/US2012/051083 dated Dec. 20, 2012.

* cited by examiner

EXPANDABLE IMPLANT

CROSS REFERENCE TO RELATED APPLICATIONS

This application claims the benefit of the filing date of U.S. Provisional Patent Application No. 61/775,909, filed Mar. 11, 2013, the disclosure of which is hereby incorporated herein by reference.

BACKGROUND OF THE INVENTION

The present invention(s) relates to expandable implants and tools for the insertion of such implants. More particularly, the invention(s) pertains to an expandable spinal implant having opposed plates, which are expandable via the interaction between a wedge member and ramped surfaces included on the plates. An insertion instrument used for implantation of the implant, and methods of utilizing the same, are also disclosed.

Common spinal maladies, such as degeneration of an intervertebral disc of the spine (commonly referred to as Degenerative Disc Disease), spondylosis, spinal stenosis, disc herniation, retrolisthesis, discogenic back pain, or other like conditions may result in substantial pain and discomfort for a patient. Frequently, conditions of this type are treated through surgical intervention, which may include replacing or removing a portion or all of the affected disc(s) and fusing the associated vertebrae through the use of an implant or other like device. In particular applications, adjacent vertebral bodies may be fused via an implant, through screw arrangements, and/or by using bone graft material to secure the vertebrae in a fixed state and promote bone growth between the vertebrae.

In replacing a diseased intervertebral disc(s) and effecting fusion, it may also be necessary to ensure that proper spacing is maintained between the vertebral bodies. Stated differently, once the implant or other like device is situated between adjacent vertebrae, the implant or device should adequately recreate the spacing previously maintained via the excised intervertebral disc (e.g., in its natural condition). Various expandable implants have been proposed for this purpose. As such, it is possible for a surgeon to adjust the height of particular intervertebral implants to intra-operatively tailor the implant height to match the natural spacing between vertebrae, or any desired implant height. This may reduce the number of different implants needed to accommodate the anatomical confines of different patients.

Various anatomical considerations are also present when implanting an implant between adjacent vertebrae and, for example, affecting fusion. In particular, certain areas of the spine (e.g., the lumbar and cervical areas) may include vertebrae that are, in their natural state, at an angle to one another. This natural angle is created by the lordosis or inward curvature of the spine at the particular location of the spine (lumbar/cervical). Thus, due to the naturally-occurring inward curvature of the spine at certain sections, adjacent vertebrae are at an angle to one another, which may be taken into account in certain applications.

Although several versions of expandable intervertebral implants are known, as detailed above, the need for an improved expandable implant remains.

BRIEF SUMMARY OF THE INVENTION

A first aspect of the present invention includes an expandable implant system comprising an implant with top and bottom plates each having a bone-contacting surface and an opposing inner surface, the inner surface of each of the top and bottom plates including a ramp surface. The system also includes an actuator situated between the inner surfaces of the top and bottom plates, the actuator being removable from between the top and bottom plates after implantation of the implant, and an expansion member removably engageable with the actuator and located between the inner surfaces of the top and bottom plates, the expansion member having angled surfaces mating with the ramp surfaces of the top and bottom plates so that, upon actuation of the actuator, the expansion member moves along a longitudinal axis of the implant to expand the top and bottom plates from a first dimension to a second greater dimension. The top and bottom plates are capable of being arranged at varying angles to one another depending on the amount of movement of the expansion member along the ramp surfaces, the angle between the top and bottom plates accommodating the natural lordosis between adjacent vertebral bodies. In one embodiment, the expansion member is also tethered to at least one of the top and bottom plates by a deformable member extending from the at least one of the top and bottom plates. At least one of the top and bottom plates may also include a relief space adapted to allow flexion of the at least one of the top and bottom plates and permit expansion of the implant from the first dimension to the second greater dimension.

A second aspect of the invention comprises an expandable implant system having an implant with top and bottom plates each having a bone-contacting surface and an opposing inner surface, the inner surface of each of the top and bottom plates including a ramp surface. The system also comprises an actuator situated between the inner surfaces of the top and bottom plates, the actuator being removable from between the top and bottom plates after implantation of the implant, and an expansion member removably engageable with the actuator and located between the inner surfaces of the top and bottom plates, the expansion member having angled surfaces mating with the ramp surfaces of the top and bottom plates so that, upon actuation of the actuator, the expansion member moves along a longitudinal axis of the implant to expand the top and bottom plates from a first dimension to a second greater dimension, wherein the top and bottom plates are arranged at varying angles to one another depending on the amount of movement of the expansion member along the ramp surfaces, the angle between the top and bottom plates accommodating the natural lordosis between adjacent vertebral bodies. At least one of the top and bottom plates may also be associated with a flange having an aperture adapted to receive a fixation member, the flange extending beyond the at least one of the top and bottom plates to prevent over insertion of the implant into an intervertebral disc space. In some cases, the ramp surfaces of the top and bottom plates and the expansion member also include teeth, the teeth of the expansion member engaging successive teeth of the ramp surfaces upon movement of the expansion member along the longitudinal axis.

A third aspect of the invention includes yet another expandable implant system comprising an implant with top and bottom plates each having a bone-contacting surface and an opposing inner surface, the inner surface of each of the top and bottom plates including a ramp surface. The system also comprises an actuator situated between the inner surfaces of the top and bottom plates, the actuator being removable from between the top and bottom plates after implantation of the implant, and an expansion member removably engageable with the actuator and located between the inner surfaces of the top and bottom plates, the expansion member having angled surfaces mating with the ramp surfaces of the top and bottom plates so that, upon actuation of the actuator, the expansion member moves along a longitudinal axis of the implant to expand the top and bottom plates from a first dimension to a second greater dimension, wherein the top and bottom plates are securable at varying angles to one another depending on the amount of movement of the expansion member along the ramp surfaces, the angle between the top and bottom plates accommodating the natural lordosis between adjacent vertebral bodies. In one embodiment of this third aspect, at least one of the top and bottom plates is also associated with a flange having an aperture adapted to receive a fixation member, the flange extending beyond the at least one of the top and bottom plates to prevent over insertion of the implant into an intervertebral disc space.

BRIEF DESCRIPTION OF THE DRAWINGS

A more complete appreciation of the subject matter of the present invention(s) and of the various advantages thereof can be realized by reference to the following detailed description in which reference is made to the accompanying drawings in which.

DETAILED DESCRIPTION

In describing the preferred embodiments of the invention(s) illustrated and to be described with respect to the drawings, specific terminology will be used for the sake of clarity. However, the invention(s) is not intended to be limited to any specific terms used herein, and it is to be understood that each specific term includes all technical equivalents, which operate in a similar manner to accomplish a similar purpose.

Figure 1:
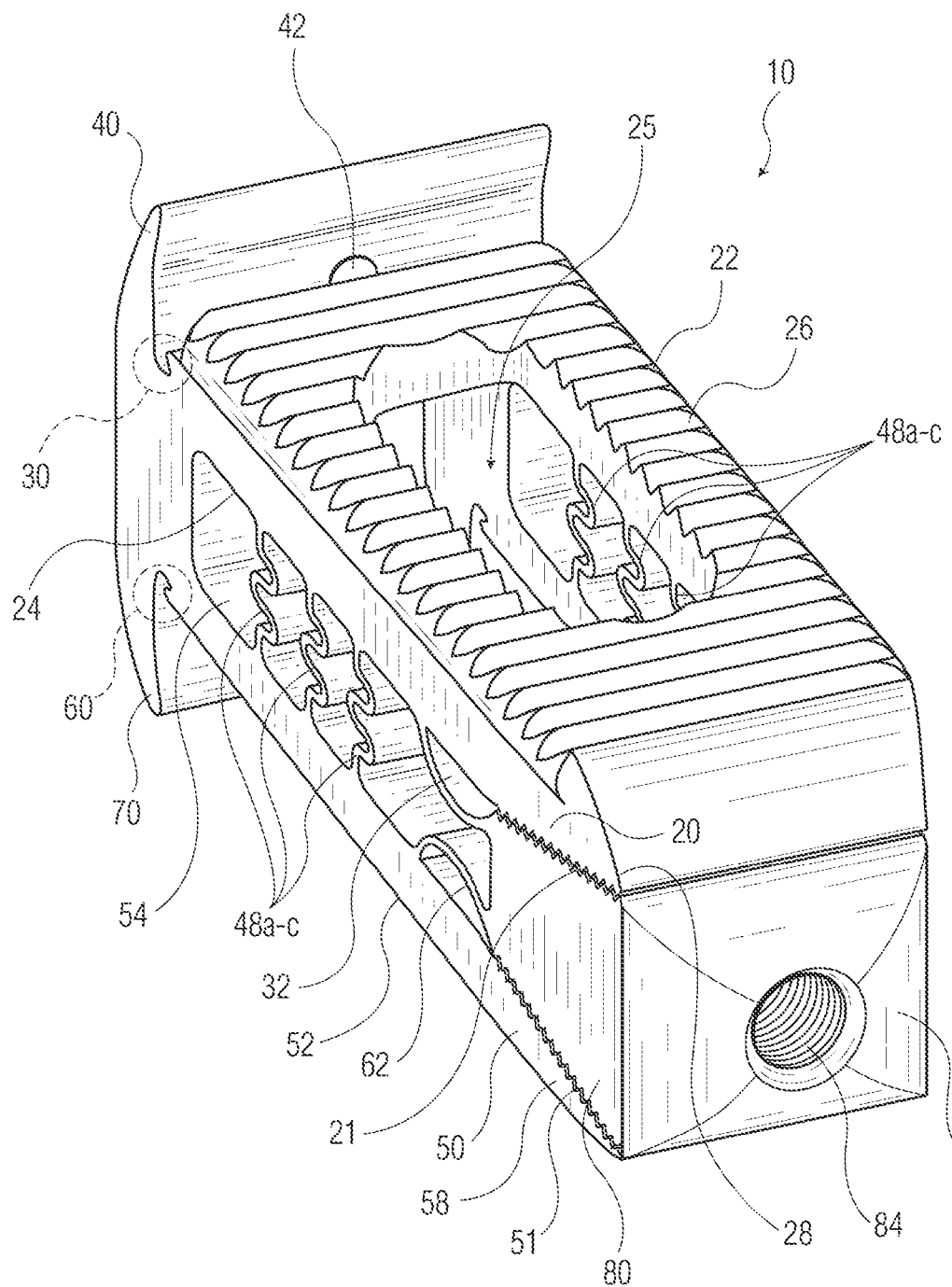
FIG. 1 is a perspective view of an expandable implant, according to one embodiment of the present invention.

Referring to FIG. 1, an implant 10 is shown as generally having top and bottom plates 20, 50 with ramp surfaces 21, 51 thereon, and at least one expansion member 80 for engaging the ramp surfaces 21, 51 and expanding the implant 10 (e.g., to place the same in a lordotic state). The implant 10 may be implanted between adjacent vertebral bodies 12, 14, as shown in FIGS. 2-5, to aid in fusion of such bodies and immobilization of the spine at the implantation site. This may help to relieve pain associated with one of the chronic degenerative spinal conditions discussed previously.

Figure 2:
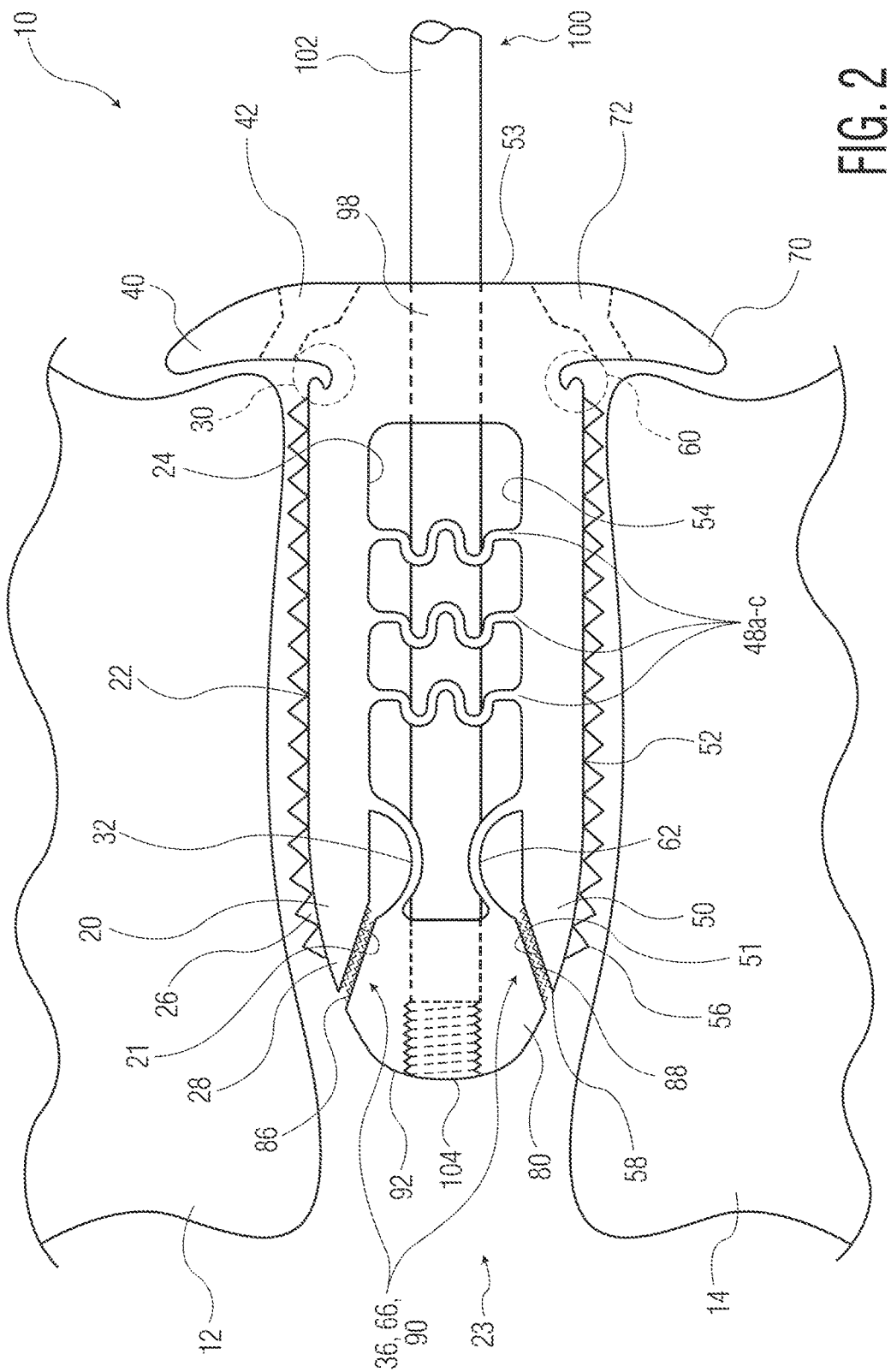
FIGS. 2-4 are side views of the steps involved in implanting the expandable implant of FIG. 1.
Figure 3:
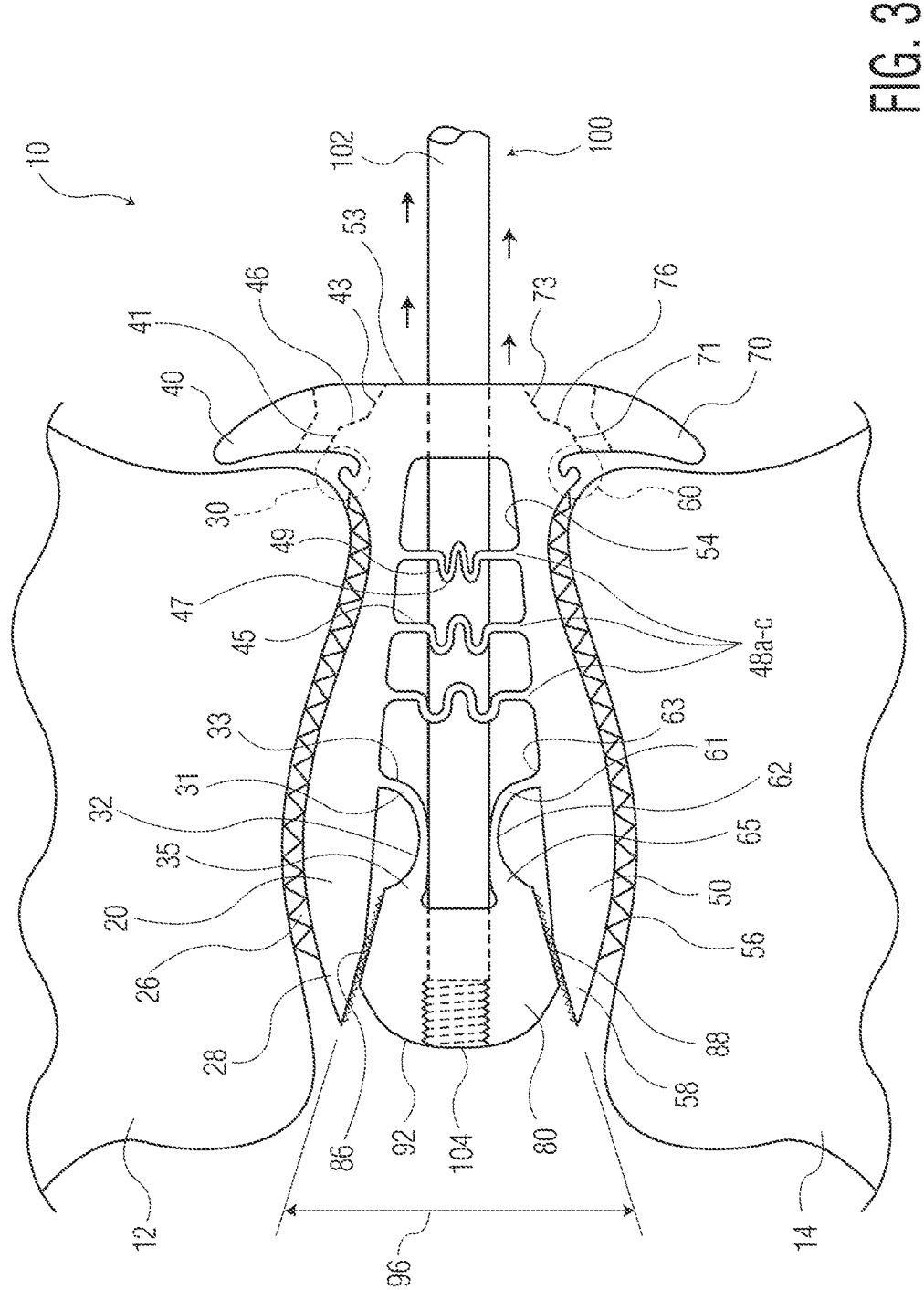
Figure 4:
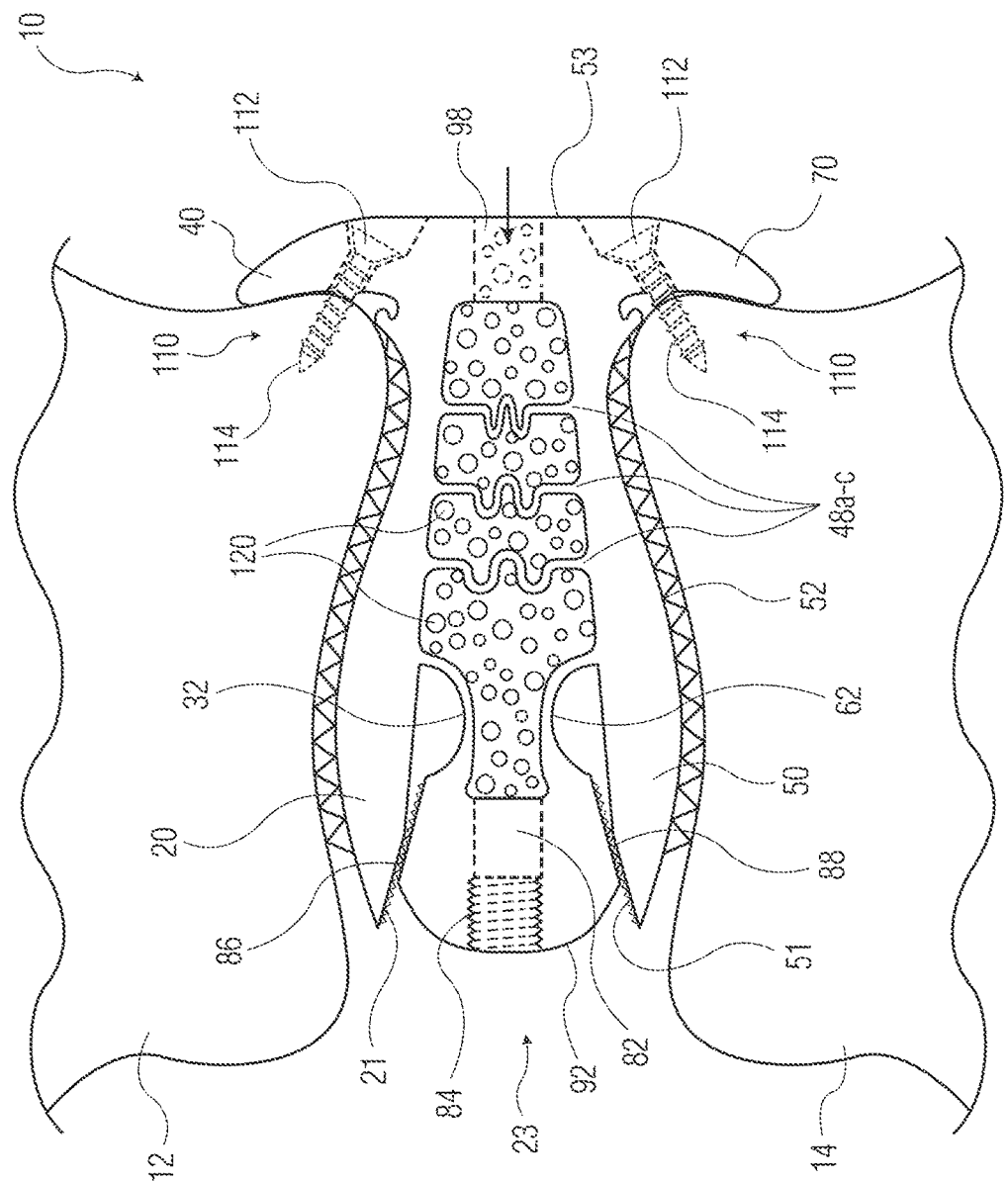

In a particular embodiment, implant 10 may have top and bottom plates 20, 50, each having a bone-contacting surface 22, 52 and an opposing inner surface 24, 54. Bone-contacting surfaces 22, 52 may, in one embodiment, be convexly shaped and include teeth or spikes 26, 56 (FIG. 2), or even other fixation devices, such as a keel(s), a projection member(s), or a combination of the foregoing. Teeth or spikes 26, 56 may aid in securing top and bottom plates 20, 50 to bone, as shown in FIGS. 2-4. Plates 20, 50 may also each include one or more vertical apertures (only one of which is shown in FIG. 1 as vertical aperture 25) for receiving bone-graft or other bone-growth material therein.

Inner surfaces 24, 54 of plates 20, 50 may face toward one another and include, in one embodiment, respective ramp surfaces 21, 51. As shown in FIG. 2, ramp surfaces 21, 51 may be angled, such that a taper 28, 58 is formed on top and bottom plates 20, 50. Further, an end 23 of implant 10 (particularly that section of implant 10 between ramp surfaces 21, 51) may remain open, allowing for flexion of plates 20, 50, while an opposing end 53 of implant 10 may remain attached or closed. In other words, at end 23 (between ramp surfaces 21, 51) top and bottom plates 20, 50 may remain unattached, while at end 53 such plates 20, 50 may be attached or connected (e.g., unitary or formed of the same material).

Plates 20, 50 of implant 10 may also be spaced from one another, as shown in FIG. 1, such that a cavity is formed between inner surfaces 24, 54; and extending through the cavity from top 20 to bottom 50 plate may be a series of deformable members or struts 48a-c. In some cases, a set of struts 48a-c may extend through the inner cavity of implant 10 on both sides of implant 10, as shown in detail in FIG. 1. In one embodiment, struts 48a-c may also be of the same structure and provide the same function as any of the struts disclosed in U.S. Pat. No. 8,267,939 to Cipoletti et al. ("the '939 patent") or U.S. Patent Pub. No. 2008/0183204 to Greenhalgh et al., the disclosures of which are hereby expressly incorporated by reference herein. Thus, struts 48a-c, in one embodiment, may be generally S-shaped and may be deformable so as to allow for contraction or expansion of implant 10 (e.g., upon movement of plates 20, 50 toward or away from one another). In particular, struts 48a-c may be designed so that they apply tension to top and bottom plates 20, 50 during and after expansion of implant 10. This encourages uniform deployment of the device, and may serve to limit distraction of plates 20, 50 of implant 10 apart, in some cases.

As shown, for example, in FIG. 3, struts 48a-c may include at least one curved section 47, which is designed to be thicker than at least one middle section 49, such that the curved section 47 may deform subsequent to the middle section 49. Each strut 48a-c may also include at least one end section 45 that is joined to one of plates 20, 50. The end section 45 may be designed in a thicker fashion as well, such that there is no deformation at end section 45 at any time during the expansion sequence. In an alternate embodiment, struts 48a-c may simply be one thickness along curved 47 and middle sections 49, and only thicker at end section 45 so as to not deform at that section 45. In any case, struts 48a-c may allow controlled expansion of plates 20, 50 of implant 10 via deformation thereof, and in certain embodiments, may limit distraction of plates 20, 50. While only six (6) struts 48a-c are shown, it is contemplated that more or less than six (6) struts 48a-c may be used.

As shown in FIGS. 1-2, a set of tethers 32, 62 may also extend from top and bottom plates 20, 50, respectively. Tethers 32, 62 may be deformable, in one embodiment, and may be connected at their ends to an expansion member 80. Like with struts 48a-c above, tethers 32, 62 may also share the same structure and function as any of the tethers disclosed in the '939 patent. As such, tethers 32, 62 may generally be deformable to allow movement of expansion member 80 with respect to plates 20, 50. Indeed, as shown in FIG. 3, tethers 32, 62 may include a section 33, 63 that is thick and connects with plates 20, 50, such that section 33, 63 does not deform during expansion of implant 10. Tethers 32, 62 may also include a separate section 31, 61 that is thinner than section 33, 63 to deform (e.g., curve or bend) upon movement of expansion member 80. Lastly, a connection point 35, 65 connecting tethers 32, 62 to expansion member 80 may also be provided, which is thicker than sections 31, 61 so as to not allow deformation at those points 35, 65. Thus, upon movement of expansion member 80, tethers 32, 62 may adequately deform to allow plates 20, 50 to separate.

Referring now to FIGS. 2-4, expansion member 80 may be in the form of a wedge with top and bottom angled surfaces 86, 88. Top and bottom angled surfaces 86, 88 may also include teeth 90 for engaging with corresponding teeth 36, 66 formed on ramp surfaces 21, 51 of plates 20, 50. Thus, a ratchet mechanism may be formed in which teeth 90 on angled surfaces 86, 88 of expansion member 80 engage successive teeth 36, 66 on ramp surfaces 21, 51 during movement of expansion member 80 and expansion of implant 10. In one embodiment, teeth 90 of expansion member 80 and teeth 36, 66 on ramp surfaces 21, 51 may be configured so that movement of expansion member 80 can proceed in only one direction (e.g., toward the inner cavity of implant 10 so as to expand the same). Thus, once expansion member 80 moves a particular amount towards the inner cavity of implant 10 to expand implant 10, expansion member 80 (and thus implant 10) may be fixed via teeth 36, 66, 90.

Expansion member 80 may further include an inner bore 82 having, in one embodiment, a threaded section 84 (FIG. 4). While threaded section 84 is shown at a distal end of inner bore 82 in the figures, it is contemplated that such threading 84 may be positioned at any point within bore 82. Expansion member 80 may also have a bulleted or blunt end 92 that is configured to facilitate insertion of implant 10 within intervertebral space. In other words, bulleted or blunt end 92 of expansion member 80 may be designed to wedge itself into the intervertebral space so that implant 10 may be easily implanted therein.

Referring again to FIG. 1, top and bottom plates 20, of implant 10 may also each include a flange 40, 70 that extends beyond plates 20, 50 to prevent over insertion of implant and allow for fixation thereof to vertebral bodies 12, 14. Indeed, a surface of flanges 40, 70 may be designed to contact portions of adjacent vertebra 12, 14, as shown in FIGS. 2-4, to prevent insertion of implant 10 beyond a desired point and allow fixation of implant to vertebrae 12, 14. In one embodiment, flanges 40, 70 may also be concavely curved so as to match the convexity of vertebrae 12, 14 adjacent flanges 40, 70; and such flanges 40, 70 may include respective apertures 42, 72 for receipt of a fixation member 110 therein (FIG. 4). Referring to FIG. 3, apertures 42, 72 through flanges 40, 70 may also be angled to direct fixation members 110 into bone at an angle, the apertures 42, 72 including a first section 41, 71 for accommodating a shaft 114 of fixation members 110 and a relatively wider second section 43, 73 for accommodating a head 112 of fixation members 110. A step 46, 76 may also be formed between sections 41, 71 and 43, 73 of apertures 42, 72. Thus, fixation members 110 may be countersunk within apertures 42, 72 so that head 112 rests on step 46, 76 and does not protrude outward from flanges 40, 70. In other embodiments, differently-configured fixation members 110 (e.g., with flat or rounded heads, different sizes, etc.) may be used, and apertures 42, 72 may be designed to accommodate such fixation members 110. Put simply, any fixation member 110 and aperture 42, 72 combination may be utilized, so long as implant 10 may be securely fixed to vertebrae 12, 14 via insertion of such fixation members 110 into apertures 42, 72.

FIGS. 1-3 also depict a relief space 30, 60 formed in each of top and bottom plates 20, 50 adjacent flanges 40, 70, the relief spaces 30, 60 facilitating flexion of plates 20, 50 during expansion of implant 10. Relief spaces 30, 60 may be formed adjacent flanges 40, 70 on either side of implant, although one set of relief spaces 30, 60 is not shown in the figures (e.g., those on the far side of implant 10 in FIG. 1). In one embodiment, relief spaces 30, 60 are in the form of a cutout or recess in plates 20, 50 that, as plates 20, 50 are separated, deforms and reduces in size to accommodate expansion of implant 10. A bore 98 may also be formed through a posterior face of implant 10, as shown in dashed lines in FIGS. 2-4 and from a posterior view in FIG. 5, such that bone-graft material 120 and/or a portion of a tool 100 (e.g., shaft 102) could be placed therethrough.

A portion of the aforementioned tool 100 is shown in FIGS. 2-3 as having a shaft 102 with a threaded end 104. Tool 100 may be inserted through bore 98 of implant 10 to connect with threaded portion 84 of expansion member 80, and is used in the expansion of implant 10, as described in more detail below.

Figure 5:
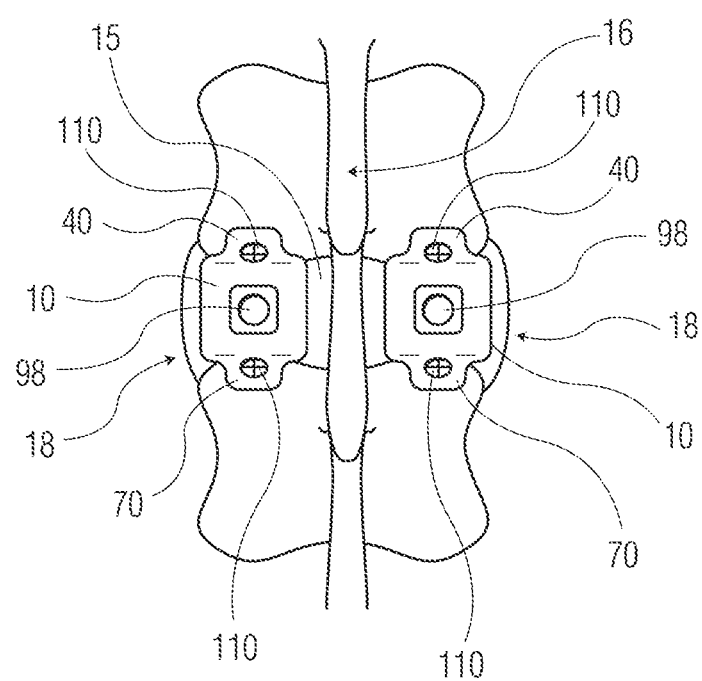
FIG. 5 is a posterior view of a portion of the spine showing two (2) of the expandable implants of FIG. 1 implanted side-by-side.

FIGS. 2-4 reflect the various method steps involved in implanting implant 10 and expanding the same. Referring to FIG. 5, a surgeon may initially resect a portion or all of an intervertebral disc 18 situated between adjacent vertebral bodies 12, 14 so as to create a space between the vertebrae 12, 14. The surgeon should be careful in this instance to not damage the spinal cord 15 (shown with disc 18 in FIG. 5). Tool 100, and in particular threaded end 104 of shaft 102 (FIG. 2), may then be connected to implant 10 at threaded portion 84 of expansion member 80, specifically via insertion of shaft 102 through bore 98 in implant 10, into and through the implant's 10 inner cavity, and into threaded portion 84 of inner bore 82 of expansion member 80. Indeed, a handle of tool 100 may simply be rotated so that threaded end 104 of shaft 102 is engaged with threaded portion 84 of expansion member 80. In this manner, tool 100 may be securely engaged with implant 10 so that implant 10 may be manipulated by the surgeon and implanted into the intervertebral disc space. Tool 100 is also removable from connection with implant 10, of course, by simply reversing the insertion steps detailed above (e.g., rotating shaft 102 in an opposite direction to disengage threaded end 104 from threaded section 84).

With tool 100 engaged to implant 10, the surgeon may then insert top and bottom plates 20, 50 within the intervertebral disc space, such that teeth 26, 56 on bone-contacting surfaces 22, 52 of plates 20, 50 engage adjacent vertebra 12, 14, as shown in FIG. 2. Due to the convexity of bone-contacting surfaces 22, 52, plates 20, 50 may also generally conform to the concave shape of the endplates of vertebrae 12, 14. Then, to expand implant 10 within the intervertebral space and maintain adequate separation between vertebrae 12, 14, the surgeon may exert a pulling force on shaft 102 of tool 100, as indicated by the arrow(s) in FIG. 3, to cause expansion member 80 to move towards the inner cavity of implant 10. At this stage, angled surfaces 86, 88 of expansion member 80 may securely engage ramp surfaces 21, 51 of plates 20, 50 to cause plates 20, 50 to distract. In a particular embodiment, since only one (1) expansion member 80 may be utilized, plates 20, 50 may predominantly distract at the open end 23 of implant 10 to create an angle 96 (FIG. 3) between plates 20, 50, which, in some cases, may be lordotic to accommodate the natural angle between vertebral bodies 12, 14. To secure implant 10 in its lordotic/expanded state, teeth 90 on expansion member 80 may engage successive teeth 36, 66 on ramp surfaces 21, 51 during movement of expansion member 80 towards the inner cavity of implant 10, and expansion member 80 may be precluded from movement in an opposite direction via the engagement between teeth 36, 66, 90.

Simultaneously, during movement of expansion member 80 and expansion of implant 10, as discussed above, tethers 32, connected to expansion member 80 may deform or bend at sections 31, 61 to accommodate sliding of expansion member 80 along ramp surfaces 21, 51. Tethers 32, 62 may also serve to ensure that teeth 90 of expansion member 80 do not disengage from teeth 36, 66 on ramp surfaces 21, 51. Indeed, after deformation of tethers 32, 62, such may exert tension on expansion member 80 towards the inner cavity of implant 10 to retain expansion member 80 in place. Also, deformable struts 48a-c may serve a similar purpose in that, during expansion of implant 10, such struts 48a-c may deform at curved 47 and/or middle 49 sections to allow distraction of plates 20, 50. And, after and/or during deformation of struts 48a-c, such may exert tension on plates 20, 50 to ensure that expansion progresses uniformly and that plates 20, 50 are compressed towards one another to retain expansion member 80 in place. Struts 48a-c may also limit distraction of plates 20, 50 in some instances. In other words, once implant 10 is expanded, struts 48a-c may be placed in tension, such that a force acts on plates 20, 50 towards the inner cavity of implant 10, thereby compressing plates 20, 50 against expansion member 80 to secure the same in place.

It should be noted, additionally, that in some embodiments there is not a need to counteract the pulling force exerted on implant 10 via tool 100 with another opposing force (e.g., by placing another portion of tool 100 or a separate tool against a surface of implant 10 adjacent flanges 40, 70). In other words, in the figures there is no portion of tool 100 (or a separate tool) that contacts implant 10 adjacent flanges 40, 70 to counteract the pulling forces exerted on implant 10 via tool 100 during expansion, although alternate embodiments of the present invention contemplate such a step. As an example, in the '939 patent it is necessary for a portion of deployment tool 350 to contact the implant 10 disclosed therein for expansion of the implant 10 to occur (e.g., second portion 354 of tool 350 contacts an exterior portion of second wedge 18 during expansion of implant 10). This is not the case with the present method or tool 100, although such a step could be performed, if desired. Indeed, in a preferred embodiment, as shown in the figures, implant 10 may sufficiently resist back-out or migration from or within the intervertebral space via the pressure exerted on plates 20, 50 by vertebrae 12, 14, and through the friction caused by teeth 26, 56 on bone-contacting surfaces 22, 52. If fixation members 110 are inserted into flanges 40, 70 prior to expansion, such fixation members 110 may help to prevent back-out and/or migration of implant 10 as well. Thus, the step of contacting implant 10 to resist back-out thereof (i.e., during pulling of tool 100) is not necessarily needed. Nonetheless, as noted above, this step is contemplated in alternate embodiments since a tool, such as deployment tool 350 of the '939 patent, is usable with implant 10 of the present invention. Indeed, with minor modifications, the tool 350 of the '939 patent would have applicability in conjunction with implant 10.

With implant 10 expanded via tool 100 and secured in its lordotic state, tool 100 may be unscrewed from engagement with expansion member 80 and withdrawn through bore 98 of implant 10, as reflected by the progression between FIGS. 3-4. After removal of tool 100, the surgeon, at his/her election, may then place bone-graft or other such material 120 through bore 98 of implant 10 and into the inner cavity of implant 10. Such bone-graft material 120 may be any material, provided the material is adapted to induce bone in-growth into implant 10 (e.g., through vertical aperture(s) 25 in plates 20, 50). Examples of such materials 120 include natural bone chips, autologous or allograft bone, or synthetic materials such as a bone-graft substitute. Bone morphogenic proteins or other osteoinductive materials may also be used in combination with or apart from material 120; and, in some embodiments, certain surfaces of implant 10 may be coated with bone-growth material to facilitate attachment to bone.

Fixation members 110, such as bone screws, pins, or other such devices, may then be driven through apertures 42, 72 in flanges 40, 70 and secured to adjacent vertebra 12, 14 to retain implant 10 within the intervertebral space. In particular, shaft 114 of fixation members 110 may be inserted through first section 41, 71 of apertures 42, 72, head 112 of fixation members 110 may rest within second section 43, 73 of apertures 42, 72 on step 46, 76, and step 46, 76 may prevent fixation members 110 from being threaded through apertures 42, 72. Alternatively, fixation members 100 may always be inserted within apertures 42, 72 in flanges 40, 70 prior to expansion of implant 10, as alluded to above. As shown in FIG. 4, fixation members 110 (via the angled nature of apertures 42, 72) may also be configured to diverge once inserted into vertebrae 12, 14 so as to resist back-out.

It is also worthwhile to note that, due to the nature of expansion member 80 and ramp surfaces 21, 51, implant 10 may be placed in varying lordotic states during expansion. In other words, due to the ratchet structure of implant 10 (i.e., teeth 90 on expansion member 80 and teeth 36, 66 on ramp surfaces 21, 51), implant 10 may be placed at varying lordotic angles, one of which is represented as angle 96 in the figures. This assists with accommodating the differences in lordosis between vertebrae 12, 14 of different patients, or at different locations within the spine. Thus, a surgeon may ultimately select the degree of lordosis required by simply moving expansion member 80 less or more along ramp surfaces 21, 51 of plates 20, 50. In a particular embodiment, the degree of lordosis that can be achieved with implant 10 is anywhere between about three to about fifteen degrees (≈3-15°). Other degrees of lordosis are also contemplated depending upon the patient being treated, of course.

In some embodiments of the aforementioned method, multiple implants 10 may be arranged side-by-side within a particular intervertebral space, as shown in FIG. 5. Indeed, two (2) implants 10 may be used (FIG. 5) to eliminate the need for posterior screws (e.g., pedicle screws). Such surgeries are sometimes referred to in the industry as a bilateral PLIF (posterior lumbar interbody fusion) stand alone surgery. Multiple levels of the spine may also receive one (1) or more implants 10, of course. It is also contemplated that, in alternate embodiments, implant 10 may be sized and shaped for implantation within the entire intervertebral space, as opposed to implanting multiple implants 10 side-by-side, as detailed above.

In still yet other embodiments, a kit of implants 10 may be offered. The kit may include implants 10 of varying sizes to accommodate differently sized patients, and in some embodiments, different implants 10 within the kit may be arrangeable at varying lordotic angles. For example, while a certain amount of implants (e.g., four (4)) within the kit may be offered at one size, and another amount (e.g., four (4)) at another smaller size, it is also contemplated that the differently-sized implants 10 within the kit (i.e., the four (4) large and small implants 10) may be expandable via expansion member 80 to or within a different range of lordotic angles. Additional sizes (e.g., large, medium, small, etc.) for implants 10 may also be offered as a kit, and the differently-sized implants 10 within the kit may be arrangeable at or within different ranges of lordotic angles, as discussed above; or in some cases, all implants 10 within the kit may be arrangeable at or within the same range of lordotic angles. Thus, varying combinations of implants 10 of differing sizes and/or that are distractible to different lordotic angles may be offered in kit form.

In the devices shown in the figures, particular structures are shown as being adapted for use in the implantation, distraction, and/or removal of an expandable implant according to the present invention(s). The invention(s) also contemplates the use of any alternative structures for such purposes, including structures having different lengths, shapes, and/or configurations. For instance, although ramp surfaces 21, 51 of plates 20, 50 and expansion member 80 include ratchet structure for expanding implant 10, other expansion mechanisms may be utilized to secure expansion member 80 (and thus implant 10) in place. As an example, roughened surfaces may be utilized in place of ratchet structure so as to secure expansion member 80 in place and distract plates 20, 50. Other like mechanisms are also contemplated.

In addition, while a certain number (e.g., six (6)) struts 48*a-c* are shown as extending from plates 20, 50, it is contemplated that any number of struts could be utilized, so long as such struts serve to perform the function(s) recited previously. And, although implant 10 is shown as utilizing only one (1) expansion member 80 to distract plates 20, 50 of implant 10 apart, additional expansion members 80 may be used. For instance, plates 20, 50 of implant 10 may be provided with multiple ramp surfaces 21, 51 and expansion members 80, each set of ramp surfaces 21, 51 and corresponding expansion member 80 being arranged alongside one another within the inner cavity of implant 10. In other words, as an example, a first set of ramp surfaces 21, 51 may be situated at open end 23 of implant 10 to interact with expansion member 80, as in the figures, while a second set of ramp surfaces (not shown) may be arranged posterior of ramp surfaces 21, 51 (e.g., within the inner cavity of implant towards flanges 40, 70), such second ramp surfaces being configured to interact with a second expansion member. Then, once implant 10 is expanded, each expansion member may interact with its respective ramp surfaces to distract plates 20, 50. In this manner, additional support may be provided to implant 10 once placed in a lordotic state (e.g., plates 20, 50 would be supported by two (2) expansion members 80 instead of one (1), as in the figures). What is more, to move multiple expansion members along their corresponding ramp surfaces, it is contemplated that shaft 102 of tool 100 may be provided with multiple threaded sections that engage a threaded bore formed in each respective expansion member. Thus, through a single pulling action, tool 100 may distract plates 20, 50 of implant 10 and move the multiple expansion members along their corresponding ramp surfaces.

As another example, although the connection between tool 100 and expansion member 80 has been discussed as being achieved via threading, it is equally contemplated that other connections are possible, such as compression-fitting, interference-fitting, or the like. For instance, shaft 102 of tool 100 may have a section that is slightly larger than a diameter of bore 98 through expansion member 80 so that, once shaft 102 is inserted into bore 98, compression results between shaft 102 and bore 98. Alternatively, shaft 102 may be provided with a set of protrusions extending from opposite sides thereof, and bore 98 may include channels or stops to engage with the protrusions. In this embodiment, shaft 102 may be inserted into bore 98 with protrusions not engaging the aforementioned channels or stops, and then be rotated so that the protrusions on shaft 102 engage the channels and form an interference fit therewith. Put simply, various other connections between shaft 102 and bore 98 are contemplated, so long as the connection allows shaft 102 to securely engage expansion member 80 and implant 10 (e.g., for insertion and expansion of implant 10) and be removable therefrom.

It is also the case that, while only one (1) relief space 30, 60 is shown on top and bottom plates 20, 50, multiple relief areas 30, 60 may be provided on plates 20, 50. Further, although only one aperture 42, 72 is described as being included on flanges 40, 70 of each plate 20, 50, multiple apertures for receipt of fixation members therein may be provided on each plate 20, 50.

As yet another example, while certain steps of the above-described method(s) may have been discussed in a particular order, it is to be understood that the order may be altered in any manner suitable to implant the implant 10 described above. Thus, the order of steps for the method(s) is not essential, and such order may be varied or changed in any manner considered suitable by one of skill in the art.

Although the invention(s) herein has been described with reference to particular embodiments, it is to be understood that these embodiments are merely illustrative of the principles and applications of the present invention(s). It is therefore to be understood that numerous modifications may be made to the illustrative embodiments and that other arrangements may be devised without departing from the spirit and scope of the present invention(s) as defined by the appended claims.

It will also be appreciated that the various dependent claims and the features set forth therein can be combined in different ways than presented in the initial claims. It will also be appreciated that the features described in connection with individual embodiments may be shared with others of the described embodiments.

The invention claimed is:

1. An expandable implant system comprising:
    an implant with top and bottom plates each having a bone-contacting surface and an opposing inner surface, the inner surface of each of the top and bottom plates including a ramp surface, wherein the implant extends along a longitudinal axis between a distal end and a proximal end, and wherein the top and bottom plates are integrally formed as a single body by being integrally joined at the proximal end;
    an actuator situated between the inner surfaces of the top and bottom plates, the actuator being removable from between the top and bottom plates after implantation of the implant; and
    an expansion member removably engageable with the actuator and located between the inner surfaces of the top and bottom plates, the expansion member having angled surfaces mating with the ramp surfaces of the top and bottom plates so that, upon actuation of the actuator, the expansion member moves in a proximal direction along the longitudinal axis of the implant to expand the top and bottom plates from a first dimension to a second greater dimension, wherein the actuator is removable from the expansion member at a plurality of positions of the expansion member along the longitudinal axis, such that the top and bottom plates are securable at varying lordotic angles to one another depending on the position of the expansion member along the longitudinal axis when the actuator is removed, the angle between the top and bottom plates accommodating a desired lordosis between adjacent vertebral bodies;

wherein at least one of the top and bottom plates includes a deformable end portion proximate the proximal end of the implant, the deformable end portion deforming during expansion of the implant from the first dimension to the second greater dimension such that the entire one of the at least one of the top and bottom plates located distally of the deformable end portion deflects outwardly about the deformable end portion.

2. The expandable implant system of claim 1, wherein the expansion member is tethered to at least one of the top and bottom plates by a deformable member extending from the at least one of the top and bottom plates.

3. The expandable implant system of claim 2, wherein the expansion member is associated with a set of deformable members that deform upon movement of the expansion member along the longitudinal axis.

4. The expandable implant system of claim 1, wherein the actuator is insertable through an opening in the implant, and a distal end of the actuator is removably engageable with the expansion member.

5. The expandable implant system of claim 4, wherein the distal end of the actuator includes threading, and the expansion member includes a threaded internal bore adapted to removably mate with the distal end of the actuator.

6. The expandable implant system of claim 1, wherein at least one of the top and bottom plates includes an aperture extending vertically though the plate to accept bone-graft or other bone-growth material.

7. The expandable implant system of claim 1, wherein the deformable end portion is adjacent a relief space that is recessed into the bone-contacting surface of the at least one of the top and bottom plates.

8. The expandable implant system of claim 1, wherein at least one of the top and bottom plates is associated with a flange extending beyond the at least one of the top and bottom plates to prevent over insertion of the implant into an intervertebral disc space.

9. The expandable implant system of claim 8, wherein the flange has an aperture adapted to receive a fixation member.

10. The expandable implant system of claim 8, wherein a relief space is adjacent the flange.

11. The expandable implant system of claim 1, wherein the ramp surfaces of the top and bottom plates and the expansion member include teeth, the teeth of the expansion member engaging successive teeth of the ramp surfaces upon movement of the expansion member along the longitudinal axis, the engagement of the teeth of the expansion member and the teeth of the ramp surfaces rendering the top and bottom plates securable at the varying lordotic angles.

12. The expandable implant system of claim 1, wherein a distal end of the actuator includes threading, and the expansion member includes a threaded internal bore adapted to removably mate with the distal end of the actuator.

13. The expandable implant system of claim 1, wherein the expansion member is associated with a set of deformable members that deform upon movement of the expansion member along the longitudinal axis.

14. The expandable implant system of claim 1, wherein the implant includes only the single expansion member and no other expansion members.

15. The expandable implant system of claim 1, wherein the bone-contacting surfaces of the top and bottom plates are each shaped convexly in a manner that conforms to a concave shape of a respective endplate of the adjacent vertebral bodies.

16. A kit including a plurality of expandable implant systems as claimed in claim 1, the top and bottom plates of the implant of a first of the plurality of expandable implant systems being securable within a first maximum range of lordotic angles, and the top and bottom plates of the implant of a second of the plurality of expandable implant systems being securable within a second different maximum range of lordotic angles.

17. The expandable implant system of claim 1, wherein the top and bottom plates are freely flexible away from one another at the distal end.

18. The expandable implant system of claim 1, wherein the actuator is insertable through an opening in the implant, and a distal end of the actuator is removably engageable with the expansion member, and wherein the opening is located at the proximal end of the implant.

19. The expandable implant system of claim 1, wherein a relief space is located at the proximal end of the implant.

20. An expandable implant system comprising:

an implant with top and bottom plates each having a bone-contacting surface and an opposing inner surface, the inner surface of each of the top and bottom plates including a ramp surface, wherein the implant extends along a longitudinal axis between a distal end and a proximal end, and wherein the top and bottom plates are integrally formed as a single body by being integrally joined at the proximal end;

an actuator situated between the inner surfaces of the top and bottom plates, the actuator being removable from between the top and bottom plates after implantation of the implant by moving the actuator in a proximal direction; and an expansion member removably engageable with the actuator and located between the inner surfaces of the top and bottom plates, the expansion member having angled surfaces mating with the ramp surfaces of the top and bottom plates so that, upon actuation of the actuator, the expansion member moves in the proximal direction along the longitudinal axis of the implant to expand the top and bottom plates from a first dimension to a second greater dimension, wherein the top and bottom plates are securable at varying lordotic angles to one another depending on the amount of movement of the expansion member along the ramp surfaces, the angle between the top and bottom plates accommodating a desired lordosis between adjacent vertebral bodies;

wherein at least one of the top and bottom plates includes a deformable end portion proximate the proximal end of the implant, the deformable end portion deforming during expansion of the implant from the first dimension to the second greater dimension such that the entire one of the at least one of the top and bottom plates located distally of the deformable end portion deflects outwardly about the deformable end portion.

21. The expandable implant system of claim 20, wherein a relief space is located at the proximal end of the implant.

22. The expandable implant system of claim 20, wherein at least one of the top and bottom plates is associated with a flange extending beyond the at least one of the top and bottom plates to prevent over insertion of the implant into an intervertebral disc space.

23. The expandable implant system of claim 22, wherein a relief space is adjacent the flange.

24. The expandable implant system of claim 20, wherein the actuator is insertable through an opening in the implant, and a distal end of the actuator is removably engageable with the expansion member.

25. The expandable implant system of claim 24, wherein the distal end of the actuator includes threading, and the expansion member includes a threaded internal bore adapted to removably mate with the distal end of the actuator.

* * * * *